US008668825B2

(12) United States Patent
Pouchoulin et al.

(10) Patent No.: US 8,668,825 B2
(45) Date of Patent: Mar. 11, 2014

(54) DEVICE AND PROCEDURE FOR EXTRACORPOREAL BLOOD TREATMENT

(75) Inventors: Dominique Pouchoulin, Tramoyes (FR); Jacques Chevallet, Sérézin du Rhône (FR)

(73) Assignee: Gambro Lundia AB, Lund (SE)

(*) Notice: Subject to any disclaimer, the term of this patent is extended or adjusted under 35 U.S.C. 154(b) by 218 days.

(21) Appl. No.: 13/062,892

(22) PCT Filed: Sep. 9, 2009

(86) PCT No.: PCT/IB2009/006801
§ 371 (c)(1),
(2), (4) Date: Mar. 23, 2011

(87) PCT Pub. No.: WO2010/029417
PCT Pub. Date: Mar. 18, 2010

(65) Prior Publication Data
US 2011/0168614 A1 Jul. 14, 2011

(30) Foreign Application Priority Data
Sep. 9, 2008 (FR) .................................... 08 04980

(51) Int. Cl.
*B01D 61/30* (2006.01)
*B01D 61/32* (2006.01)
*A61M 1/14* (2006.01)
(52) U.S. Cl.
USPC ........................................................ 210/87
(58) Field of Classification Search
USPC .............. 210/87, 96.2, 198.1, 321.6, 321.65, 210/645–647, 929, 85, 103, 143, 101, 137; 604/4.01, 5.01, 6.01, 6.09, 6.11, 19, 604/27, 65–67; 700/29–31, 273, 282; 702/45; 703/2
See application file for complete search history.

(56) References Cited

U.S. PATENT DOCUMENTS 4,500,309 A 2/1985 Diederich et al.
6,635,026 B1 10/2003 Béné
(Continued)

FOREIGN PATENT DOCUMENTS

EP 1 430 920 A1 6/2004
EP 1 897 535 A1 3/2008
(Continued)

OTHER PUBLICATIONS

Booklet, "Acute Therapy Systems—Regional Anticoagulation with multiFiltrate Ci-Ca—Basic Principles and Clinical Implementation", Fresenius Medical Care, 2006, 14 pages.
(Continued)

*Primary Examiner* — Joseph Drodge
(74) *Attorney, Agent, or Firm* — Pearne & Gordon LLP

(57) ABSTRACT

An extracorporeal blood treatment device including a filter having a primary and a secondary chamber separated by a semi-permeable membrane, a withdrawal line connected to the primary chamber and associated to a first pump, a return line at the outlet of the primary chamber, a first pre-infusion line (109) connected to a citrate container on the withdrawal line (106), associated to a second pump, a first post-infusion line connected to a calcium solution container and to the return line, and associated to a third pump, an effluent line from the secondary chamber connected to a drain pipe and associated to a fourth pump, a CPU including first means programmed to receive the signal output by the pumps and second means programmed to control the third post-infusion pump (121) as a function of the input flow rate, effluent liquid flow rate, and anticoagulation liquid flow rate.

20 Claims, 6 Drawing Sheets

(56) References Cited

U.S. PATENT DOCUMENTS

| | | |
|---|---|---|
| 6,911,007 B2 | 6/2005 | Nier et al. |
| 7,029,456 B2 | 4/2006 | Ware et al. |
| 7,067,061 B2 * | 6/2006 | Bosetto et al. ............ 210/647 |
| 7,540,958 B2 * | 6/2009 | Chevallet et al. ........... 210/258 |
| 7,785,463 B2 * | 8/2010 | Bissler et al. ............ 210/143 |
| 8,133,194 B2 * | 3/2012 | Szamosfalvi et al. ....... 604/6.07 |
| 8,211,048 B2 * | 7/2012 | Szamosfalvi et al. ....... 604/5.04 |
| 2001/0037968 A1 | 11/2001 | Bene et al. |
| 2002/0107469 A1 | 8/2002 | Bolan et al. |
| 2003/0045827 A1 | 3/2003 | Nier et al. |
| 2005/0004502 A1 * | 1/2005 | O'Mahony et al. .......... 604/4.01 |
| 2007/0062861 A1 | 3/2007 | Lannoy |
| 2007/0066928 A1 | 3/2007 | Lannoy |

FOREIGN PATENT DOCUMENTS

| | | |
|---|---|---|
| WO | 91/06326 A1 | 5/1991 |
| WO | 2007/038347 A1 | 4/2007 |
| WO | 2007/062197 A1 | 5/2007 |
| WO | 2007/101064 A2 | 9/2007 |
| WO | 2009/026603 A1 | 3/2009 |

OTHER PUBLICATIONS

Wynckel A et al., "Assessment of Acetate Free Continuous Veno-Venous Hemofiltration in Acute Renal Failure", Asaio Journal, 1998, XP-000802382, pp. M606-M609.

* cited by examiner

DEVICE AND PROCEDURE FOR EXTRACORPOREAL BLOOD TREATMENT

TECHNICAL FIELD OF THE INVENTION

The present invention concerns a procedure and a device for extracorporeal blood treatment using citrate anticoagulation. This treatment may be applied in particular to continuous blood treatment administered in intensive care units.

Extracorporeal blood treatment implies withdrawing patient's blood, treating blood outside of the patient, and sending the treated blood back to the patient. Extracorporeal blood treatment is typically used to extract undesirable substances or molecules from the patient's blood, and/or to add materials or molecules beneficial to the blood. Extracorporeal blood treatment is used in patients incapable of eliminating efficiently substances from their blood, such as patients suffering from temporary or permanent kidney failure. For example, these and other patients may receive an extracorporeal blood treatment to add or eliminate substances from their blood, to maintain an acid/base balance, or to eliminate excessive body fluids.

A typical extracorporeal blood treatment comprises withdrawing the patient's blood in a continuous flow, and introducing the blood in a primary chamber of a filtration unit, hereinafter referred to as filter, where blood passes through a semi-permeable membrane. On the other side of the membrane, in a secondary chamber, a dialysis liquid flows. The semi-permeable membrane lets substances pass, in a selective way, into the blood through the membrane, from said secondary chamber to said primary chamber, and also lets substances pass, in a selective way, into the secondary chamber through the membrane from the blood in the primary chamber, depending upon the type of treatment.

A number of different types of extracorporeal blood treatments may be realized.

In ultrafiltration (UF) treatments, excess water is withdrawn from the blood by passage through the membrane toward the secondary chamber. The passage occurs by transmembrane pressure gradient between the primary chamber and the secondary chamber.

In hemofiltration (HF) treatments, high volume ultrafiltration is performed to remove solutes by convection and fluid is added to the blood, typically by introducing it, either before ("pre-infusion"), or after ("post-infusion") its passage through the filter, and before blood is sent back to the patient. The fluid infusion balances fluid loss.

In hemodialysis (HD) treatments, a secondary fluid containing beneficial substances is introduced in the secondary chamber of the filter. Undesirable blood substances cross the semi-permeable membrane by diffusion, due to a substance concentration gradient between the blood and the secondary fluid called dialysis liquid, and beneficial substances of the secondary fluid may cross the membrane and enter the blood.

In hemodiafiltration (HDF) treatments, blood and secondary fluid exchange their substances as in HD, solutes are also additionally removed by convection and, in addition, substances are added to blood, typically by introducing a fluid in the treated blood before it is sent back to the patient as in hemofiltration.

With these treatments, in the secondary chamber of the filter, the secondary fluid receives undesirable blood substances through the membrane. This fluid is then extracted from the filter: it is commonly referred to as used dialysis liquid or effluent liquid, and it is brought toward an open drain pipe or toward a closed collection device, such as a bag.

In order to carry out one of such extracorporeal blood treatments, blood is normally continuously withdrawn, through a withdrawal line, from an artery of the patient and, after being treated, is returned to the patient through a return line.

Carrying out an extracorporeal blood treatment (generically, covering all possible aforementioned methods) requires to anticoagulate the circulating blood in the extracorporeal circulation line in order to avoid blood coagulation upon contact with synthetic materials (circulation lines, semi-permeable membrane). Most often, this anticoagulation is achieved by using heparin, known for its anticoagulant properties. Heparin is injected as pre-infusion in the withdrawal line of the device, and is present in the whole extracorporeal blood circuit, from pre-infusion to blood reinjection into the patient. Therefore, doses of heparin are administered to the patient through blood return line. And, even though it is necessary to prevent coagulation in the extracorporeal circulation line, in some cases the possibility of bleeding for the patient due to the administered heparin may be a serious risk. This is particularly true in patients with strong hemorrhagic risk (for example in the days that follow a major surgical intervention) or patients with heparin hypersensitivity. Therefore, heparin anticoagulation treatment is not always applicable or the best for the patient.

In order to avoid blood coagulation, at the time of an extracorporeal blood treatment, it is known that citrate ions may be used as alternative anticoagulants instead of heparin. Citrate ions, added to blood in the extracorporeal circuit before it enters the filtration unit, are active as anticoagulants. Indeed this anticoagulant activity derives from the chelation of calcium caused by citrate ions and from the fact that ionized calcium ions are essential 'elements' of the coagulation cascade. During hemodialysis some of the citrate ions cross the filter. When reaching the patients systemic circulation, the citrate-calcium complexes are quickly metabolized in bicarbonate ions, releasing the ionized calcium in the bloodstream. Therefore citrate ions are active as anticoagulants only in the extracorporeal circuit.

Thus, the risk of bleeding complications due to systemic anticoagulation is avoided.

There are two main forms of calcium in a patient's blood: ionized calcium Ca2+ and protein-chelated calcium "CaProt". Principally in protein-chelated calcium "CaProt", calcium is bound to serum albumin which is the main protein carrier (Ca– albumin).

Ca2+ ions are a component of the coagulation cascade: above a certain concentration Ca2+ ions ensure proper coagulation function.

When blood circulates in the extracorporeal blood circuit, the coagulation function may be cancelled by decreasing blood Ca2+ ion concentration below a certain threshold (about 0.3-0.4 mmol/L). This is done by injecting pre-diluted citrate near the vascular access of the withdrawal line in the extracorporeal blood circuit. Citrate will react with Ca2+ ions and "CaProt" to generate a third form of calcium: citrate-chelated calcium or "CaCit". These reactions will decrease Ca2+ ion concentration. These three forms of calcium will re-enter into the patient blood system through the return line of the extracorporeal blood circuit.

The metabolism of citrate will then release ionized Ca and bicarbonate. Citrate metabolism occurs mainly in the liver (but also in kidney and skeletal muscles) and one citrate molecule is metabolized into three bicarbonate releasing ionized calcium. Therefore Ca2+ concentration increases and coagulation processes return to normal in the patient.

But a problem remains in the extracorporeal blood circuit: after citrate infusion, it was observed that part of the calcium crosses the semi-permeable membrane of the extracorporeal blood circuit, and is not returned to the patient. It was observed that, for citrated blood, more calcium is passing through said membrane than for non-citrated blood, and thus will not be returned to the patient. Therefore, direct injection of calcium into the patient's blood or in the return line of the extracorporeal circuit alleviates such calcium loss.

In addition, citrate injection alters the patient's acid-base balance; adjustment of bicarbonate concentration in dialysis liquid or bicarbonate infusion rate in post-dilution are known means to maintain the desired balance.

With regard to regional citrate anticoagulation, empirical "recipes" to control citrate and calcium injection are used today:

A first empirical method called "Method of Niles" in CVVH (continuous veno-venous hemofiltration—CVV designating a treatment by withdrawing from and returning to a patient's vein) provides for citrate control, injecting a quantity of citrate proportional to the blood flow of the patient after pre-dilution, according to a table of suggested values. This method provides for controlling the injected calcium through a line distinct from the extracorporeal blood circuit according to a table of suggested values matching the blood flow.

A second empirical method called "Method of Mehta" controls citrate in two ways:
1) citrate injection according to post-filter calculated quantities of activated coagulation time (ACT), according to a table of suggested values,
2) citrate injection according to ionized calcium concentration measured post-filter, according to a table of suggested values.

For controlling calcium, this "Mehta method" includes a calcium injection according to peripheral (body) measured ionized calcium, according to a table of suggested values.

Additionally, Patent Application US2007/0062861 introduces citrate anticoagulation in continuous dialysis controlling for citrate flow rate and injected calcium flow rate as a function of the evolution during the treatment of the citrate container weight and the calcium container weight, and of preprogrammed values.

U.S. Pat. No. 4,500,309 relates to citrate anticoagulation hemodialysis. It describes that the quantity of injected citrate in the withdrawal line should be empirically at about 10 mmol of citrate anion per liter of blood, and that the quantity of injected calcium should be the amount of lost calcium. Calcium clearance, i.e. the blood volume from which calcium is completely eliminated by the filtration unit per unit of time, has been measured under various circumstances (flow rates, citrate) and is reproducible with a maximal value of 100 ml/min. Based on said clearance and on the blood flow rate in the withdrawal line, the quantity of calcium lost per time unit was calculated, and used to control the amount of calcium to be injected.

Application US2002/0107469 introduces an apheresis blood treatment with regional citrate anticoagulation, and states as obvious that the injection of calcium called antidote to be introduced depends on the quantity of citrate introduced, because the calcium is injected to restore the balance tilted by citrate injection.

Finally, the booklet "Regional anticoagulation with Multifiltrate Ci-Ca—basic principles and clinical implementation" published by the company Fresenius Medical Care suggests in the specific case of CVVHD (continuous veno-venous hemodialysis) to control the citrate flow proportional to the blood flow rate and to control the calcium flow rate proportional to the effluent flow rate.

Among all controls presented above of calcium flow rate to be injected directly into the patient or in the return line of the extracorporeal blood circuit, no method presents both sufficient precision and sufficient reactivity during extracorporeal blood treatment. In addition, the controls presented above do not apply to all modes of treatment by continuous blood treatment in intensive units provided above: the HD, HF, HDF, UF modes and supported by a single device.

The object of the present invention is to offer a method for controlling the injected calcium rate in a continuous extracorporeal blood circuit using regional citrate anticoagulation and solving the problems listed above.

Therefore, the invention concerns a device for extracorporeal blood treatment 101 comprising a filter 102 having a primary 103 and a secondary 104 chamber separated by a semi-permeable membrane 105, a withdrawal line 106 connected to the primary chamber 103 of the filter 102, the withdrawal line 106 is operationally associated to a first means for regulating blood flow rate Qb 115 (or $Q_{pw}$, i.e. plasma water flow rate or $Q_p$, i.e. plasma flow rate), a return line 108 at the outlet of the primary chamber 103 of the filter 102, a first pre-infusion line 109 connected to a local anticoagulation substance container 131 and connected to the withdrawal line 106, and operationally associated to a second means for regulating anticoagulation liquid flow rate Qpre1 119, a first post-infusion line 112 connected to a container of a solution at least partially restoring blood ionic balance 133 and connected to the return line, and operationally associated to a third means for regulating the ionic balance restoring solution flow rate Qpost1 121, an effluent line 110 connected at the outlet of the secondary chamber 104 of the filter 102, connected to a drain pipe, and operationally associated to a fourth means for regulating effluent liquid flow rate Qeff 123, said device containing a CPU 125 including first means programmed to receive signal output by at least one of the means for regulating liquid flow rates 115, 119, 121, 123, and second means programmed to control at least the third means for regulating the ionic balance restoring solution flow rate Qpost1 121 as a function of the input flow rate equal to the blood flow rate Qb, of effluent liquid flow rate Qeff, and of anticoagulation liquid flow rate Qpre1.

The invention also concerns a procedure for extracorporeal blood treatment in a blood treatment device 101 containing a filter 102 having a primary 103 and a secondary 104 chamber separated by a semi-permeable membrane 105, a withdrawal line 106 connected to primary chamber 103 of the filter 102, withdrawal line 106 is operationally associated to a first means for regulating blood flow rate Qb 115, a return line 108 at the outlet of the first primary 103 of filter 102, a first pre-infusion line 109 connected to a local anticoagulation substance container, and connected to the withdrawal line 106, and operationally associated to a second means for regulating anticoagulation liquid flow rate Qpre1 119, a first post-infusion line 112 connected to a container of a solution at least partially restoring the ionic balance of blood directly infusing into the patient or, alternatively, connected to the return line and operationally associated to a third means for regulating the ionic balance restoring solution flow rate Qpost1 121, an effluent line 110 connected at the outlet of the secondary chamber 104 of the filter 102, connected to a drain pipe and operationally associated to a fourth means for regulating the effluent liquid flow rate Qeff 123, a CPU 125 to receive a signal from at least one of the flow rate regulating means, and to control at least one of the flow rate regulating means, the procedure comprising the following steps:

a) receiving the signal output by at least one of the liquid flow rate regulating means 115, 119, 123, and b) controlling at least the third means for regulating the ionic balance restoring solution flow rate Qpost1 121 as a function of the input flow rate equal to the blood flow rate Qb, of effluent liquid flow rate Qeff and of anticoagulation liquid flow rate Qpre1.

APPROACH OF THE INVENTION

In order to arrive to the invention, the inventors have thought through the phenomena of compound transports for each proposed mode of treatment, the associated flow rates, as well as the chemical reactions occurring in the extracorporeal blood circuit in relation to at least the calcium component. The inventors conducted tests, made models of the extracorporeal circuit as a function of the various modes of treatment proposed with a single blood treatment device, starting from adequate choices and hypotheses.

The inventors have always used a model at equilibrium in the patient. The set of chemical reactions is considered and the inventors tried to calculate them using the best adjusted approximation possible and/or a model of the calcium quantity lost through the filtration unit.

In the coagulation cascade, one of the factors is directly linked to ionized calcium in plasma. In case of absence of ionized calcium, the coagulation chain is blocked and coagulation no longer occurs. To obtain it, a local anticoagulation branched substance (e.g. citrate as sodium salt or citric acid) is introduced into the blood. The sodium citrate molecule ($CitNa_3$) exchanges sodium ions for calcium ions and a part of the citrate becomes chelated.

The calcium is initially present in the blood under two main forms: ionized calcium (about 1.1 mmol/L ionized) and protein-chelated calcium including albumin (about 0.9 to 1 mmol/L). Such protein-chelated calcium ions are a natural calcium reserve and may be released in the plasma to maintain an ionized calcium concentration sufficient for adequate coagulation. To neutralize calcium in plasma, citrate needs therefore to be introduced not only to chelate ionized calcium but also protein-bound calcium that will be released in plasma. The amount of citrate introduced could also take into account magnesium whose chelating properties with citrate are similar to those of calcium.

Taking into account the known literature, the inventors consider that proper anticoagulation requires a level of ionized calcium ranging between about 0.2 mmol/L and 0.4 mmol/L, and for example equal to 0.4 mmol/L. In order to reach such calcium level, ionized calcium and part of protein-bound calcium in plasma need to be chelated.

The salting out of calcium ions depends on the initial concentration of each form of calcium. A model of "CaProt" salting out into ionized Ca as a function of ionized calcium concentration was made according to all components present and considering all possible reactions (it is anyway clear that a simplified model may also be used avoiding the need of the following equations, as it will be explained in the following part of the description), starting from the hypothesis that chemical balance is reached as follows:

Ca2++Cit3- ↔ CaCit-(log K=3.364)

Ca2++2Cit3- ↔ CaCit2 4-(log K=4.964)

Mg2++Cit3- ↔ MgCit-(log K=3.333)

Mg2++2Cit3- ↔ MgCit2 4-(log K=5.126)

Ca2++HCO3- ↔ CaHCO3+(log K=0.8)

Mg2++HCO3- ↔ MgHCO3+(log K=0.8)

Alb21-+Ca2+ ↔ CaAlb19-(log K=3.0)

CaAlb19-+Ca2+ ↔ Ca2Alb17-(log K=5.9)

Ca2Alb17-+Ca2+ ↔ Ca3Alb15-(log K=8.8)

Ca3Alb15-+Ca2+ ↔ Ca4Alb13-(log K=11.7)

Ca4Alb13-+Ca2+ ↔ Ca5Alb11-(log K=14.5)

Ca5Alb11-+Ca2+ ↔ Ca6Alb9-(log K=17.2)

Ca6Alb9-+Ca2+ ↔ Ca7Alb7-(log K=19.9)

Ca7Alb7-+Ca2+ ↔ Ca8Alb5-(log K=22.5)

Ca8Alb5-+Ca2+ ↔ Ca9Alb3-(log K=25)

Ca9Alb3-+Ca2+ ↔ Ca10Alb-(log K=27.4)

H++HCO3- ↔ CO2(g)+H2O(log K=6.06)

HCO3- ↔ CO3 2-+H+(log K=-9.77)

H++Cit3- ↔ HCit2-(log K=5.5)

H++HCit2- ↔ H2Cit-(log K=9.75)

H++H2Cit- ↔ H3Cit(log K=12.4)

The results are given in the Graph:

From the Graph (see FIG. 5) resulting from this model, one deducts the citrate concentration needed to obtain an ionized calcium concentration equal to 0.4 mmol/L or less. The technique would therefore comprise introducing at least the citrate amount necessary and sufficient from the model to obtain 0.4 mmol/L of ionized calcium.

Because the semipermeable membranes are designed not to allow for albumin transfer to effluent liquid; only the calcium species others than "CaProt" may be transferred into the effluent. Data from the 'Graph' then allow defining the fraction of Ca that may be transferred.

In detail the amount of calcium that may be extracted through the semipermeable membrane is no longer about 60% (as in situation with no regional citrate anticoagulation) but rises up to 90%.

Ca2+ ions and CaCit are of small size and practically are the only species passing through the membrane. Therefore the fraction of extractable calcium, i.e. calcium capable to cross the membrane, is calculable from the concentrations modeled at equilibrium, and is equal to:

FRACTION=([Ca2+]+[CaHCO3]+[CaCit])/([Ca2+]+ [CaHCO3]+[CaCit]+[CaProt])  (equation 0)

In a further approximation, it is possible to ignore [HCO3).

FRACTION=([Ca2+]+[CaCit])/([Ca2+]+[CaCit]+ [CaProt])  (equation 0')

In the simplest approximation the FRACTION may also be taken as constant.

The concentrations involved may be measured and/or calculated by modeling according to the above described set of equations which should be partially or completely considered according to the selected degree of precision.

In addition, the inventors determined that for 'standard' CRRT conditions with effluent liquid flow rate Qeff 1000-3000 ml/h and filter surface area >0.5 m² and continuous (blood treatment with no interruptions) purification corresponding to intensive care and originating from the fact that calcium transferable species (ionized, CaCit, CaHCO3 mainly) are small molecules (mw<400 g/mole), total calcium clearance—i.e. the volume of blood where the calcium will be completely extracted by unit of time—may be evaluated by (with correction in the case of pre-dilution):

$$Ca\ Clearance = Qb/(Qb+Qpre) \times Qeff \quad \text{(equation 1)}$$

With Qpre=Qpre1+Qpre2

In addition, the effluent liquid flow rate may be defined by:

$$Qeff = Qdial + Qpre1 + Qpre2 + Qpost2 + Qpost1 + Qwl$$

Depending upon the different modes of treatment suggested,

Qb=flow rate of blood entering the withdrawal line,

Qpre1=flow rate of anticoagulation liquid or flow rate of the local anticoagulation solution, Qpre2=flow rate of replacement solution at pre-infusion on the withdrawal line, Qdial=flow rate of dialysis liquid entering the secondary chamber of the filter, Qeff=flow rate of effluent liquid at the outlet of the secondary chamber of the filter, Qpost1=flow rate of the ionic balance restoring solution or flow rate of the calcium or the solution infusion at least partially restoring the ionic balance, Qpost2=flow rate of replacement solution at post injection (post infusion) on the return line, Qwl=flow rate of removed fluid from the patient, Therefore calcium loss in mole/min which needs to be compensated by infusion of the calcium solution to restore the balance is:

$$Ca\ Loss = [Ca\ Tot] * FRACTION * Ca\ Clearance$$

With

[Ca Tot] the total calcium concentration in the systemic circuit, such as calcium concentration modeled at equilibrium.

FRACTION=fraction of calcium that may be extracted through the membrane, which may be known notably by modeling, and which is equal to the sum of ionized calcium and citrate calcium divided by the calcium contained in the patient (or, in a simplified equation, is considered constant).

Ca Clearance may be calculated by approximation following the selected mode of treatment.

Knowing the calcium concentration [CaPost1] in a syringe or in a calcium-containing bag, the ionic balance restoring solution flow rate Qpost1 of the syringe containing calcium or of the operational pump on the calcium infusion line connected to the container of calcium solution, and connected to the return line to be controlled is deduced as follows:

$$Qpost1 = [Catot] \times FRACTION \times Ca\ Clearance/[Capost1] \quad \text{(equation A)}$$

$$Qpost1 = [CaTot] \times FRACTION \times Qb/(Qb+Qpre) \times Qeff/[Capost1]$$

(equation A') in a chosen approximation of calcium clearance.

In conclusion regarding the inventors' approach:

the control of calcium to be reinjected is not obtained just "empirically" but through calculation following modeling of the reactions in the blood circulation, or by approximation of calcium clearance, notably according to the flow rates. This demonstrates that, contrary to some publications, the amount of calcium to be reinjected is not proportional to the citrate dose or not just linked to the citrate dose.

the control of calcium to be reinjected is advantageously applicable to CVVH (continuous veno-venous HF), CVVHD (continuous veno-venous HD), and CVVHDF (continuous veno-venous HDF), with pre and/or post-dilution.

the control of calcium to be reinjected may be simplified according to some features of the chosen treatment or to some adequately chosen approximations.

Choices for simplifying the equation may be considered to avoid a number of operations. Therefore, the applicant considered controlling calcium flow rate according to flow rates known from measuring or controlling as follows:

$$Ca\ clearance = Qb/(Qb+Qpre) \times Qeff$$

$$Qpre = Qpre1 + Qpre2$$

Where Qb is the blood flow rate, Qpre is the total pre-infused liquid, Qpre1 is the flow rate of anticoagulation liquid and Qpre2 is flow rate of replacement solution at pre-infusion on the withdrawal line.

Indeed,

It is possible to consider the ionic balance restoring solution flow rate Qpost1 solely proportional to effluent liquid flow rate Qeff but it could be too approximate, and would probably be valid only in some modes, and with only specific values of citrate concentration, considering equation Qb/(Qb+Qpre)×Qeff (where Qb is the blood flow rate, Qpre is the total pre-infused liquid, Qpre1 is the flow rate of anticoagulation liquid and Qpre2 is flow rate of replacement solution at pre-infusion on the withdrawal line) enables to apply the invention to all modes of continuous renal therapy in intensive care units: CVVH, CVVHD, CVVHDF.

this mode follows the hypothesis that the effluent liquid is in balance with the solution reentering the filtration unit, and therefore takes into account pre and/or post filter modifications or dilutions, which are:

any citrate concentration (not necessarily high), a modification of citrate prescription, a modification of the blood flow rate during treatment, a modification of the citrate flow rate during treatment, a modification of the pre-infusion replacement solution flow rate during treatment.

This invention helps considering modifications during treatment and deemed having the highest influence on calcium evolution.

Of course, the most precise mode for controlling the solution flow rate and at least partially restoring ionic balance according to the invention will be the mode using the following equation:

$$Qpost1 = [Catot] \times ([Ca2+] + [CaHCO3] + [CaCit])/([Ca2+] + [CaHCO3] + [CaCit] + [CaProt]) \times Qb/(Qb+Qpre) \times Qeff/[Capost1]$$

Where the terms of the above equation are those previously defined with respect to equation 0, equation 1 and equation A.

During treatment, it allows updating flow rates and concentrations, modeled or even measured.

Again, in a later approximation of this equation, it is possible to ignore [HCO3] molecules.

The invention considers all treatment modes and their approximation so as to deduce a control of the calcium to be injected. Those skilled in the art will be able to deduce the control according to the invention based on having calcium directly injected in the patient through a syringe independent from the extracorporeal blood circuit (also in this case ionic balance restoring solution flow rate Qpost1 may be included in the fluid balance of the extracorporeal flow rates) or injected in the return line of the extracorporeal blood circuit (with presence of a ionic balance restoring solution flow rate Qpost1 in the balance of the extracorporeal circuit flow rates as well), and able to introduce a supplementary dilution in the return line. For a same treatment, injection in the return line of the extracorporeal circuit is represented in FIG. 1, whereas direct injection to the patient is represented in FIG. 1'. Although not illustrated, the same principle holds for the treatments represented in FIGS. 2, 3, 4 that may have ionic balance restoring solution directly injected in the patient, and not in the extracorporeal circuit return line.

BRIEF DESCRIPTION OF THE DRAWINGS

One may refer to the attached drawings wherein:

FIG. 1 represents the hydraulic diagram of the circuit for SCUF treatment mode by convection with the injection of an ionic balance restoring solution injected in the extracorporeal circuit return line.

FIG. 1' represents the hydraulic diagram of the circuit for SCUF treatment mode by convection with the injection of the ionic balance restoring solution directly in the patient;

One may describe the different treatment modes proposed by the extracorporeal blood treatment machine and merely described above as follows:

in hemofiltration mode: with dialysis liquid flow rate Qdial equal to 0 and with at least one of pre-infusion replacement solution flow rate Qpre2 and post-infusion replacement solution flow rate Qpost2 different from zero.

in hemodialysis mode: with dialysis liquid flow rate Qdial different from 0 and pre-infusion replacement solution flow rate Qpre2 equal to 0 and post-infusion replacement solution flow rate Qpost2 equal to 0.

in hemodiafiltration mode: with dialysis liquid flow rate Qdial different from 0 and with at least one of pre-infusion replacement solution flow rate Qpre2 and post-infusion replacement solution flow rate Qpost2 different from zero.

in ultrafiltration mode: dialysis liquid flow rate Qdial equal to 0, fluid removal flow rate Qwl different from 0, and pre-infusion replacement solution flow rate Qpre2 equal to 0 and post-infusion replacement solution flow rate Qpost2 equal to 0.

Figure 1:
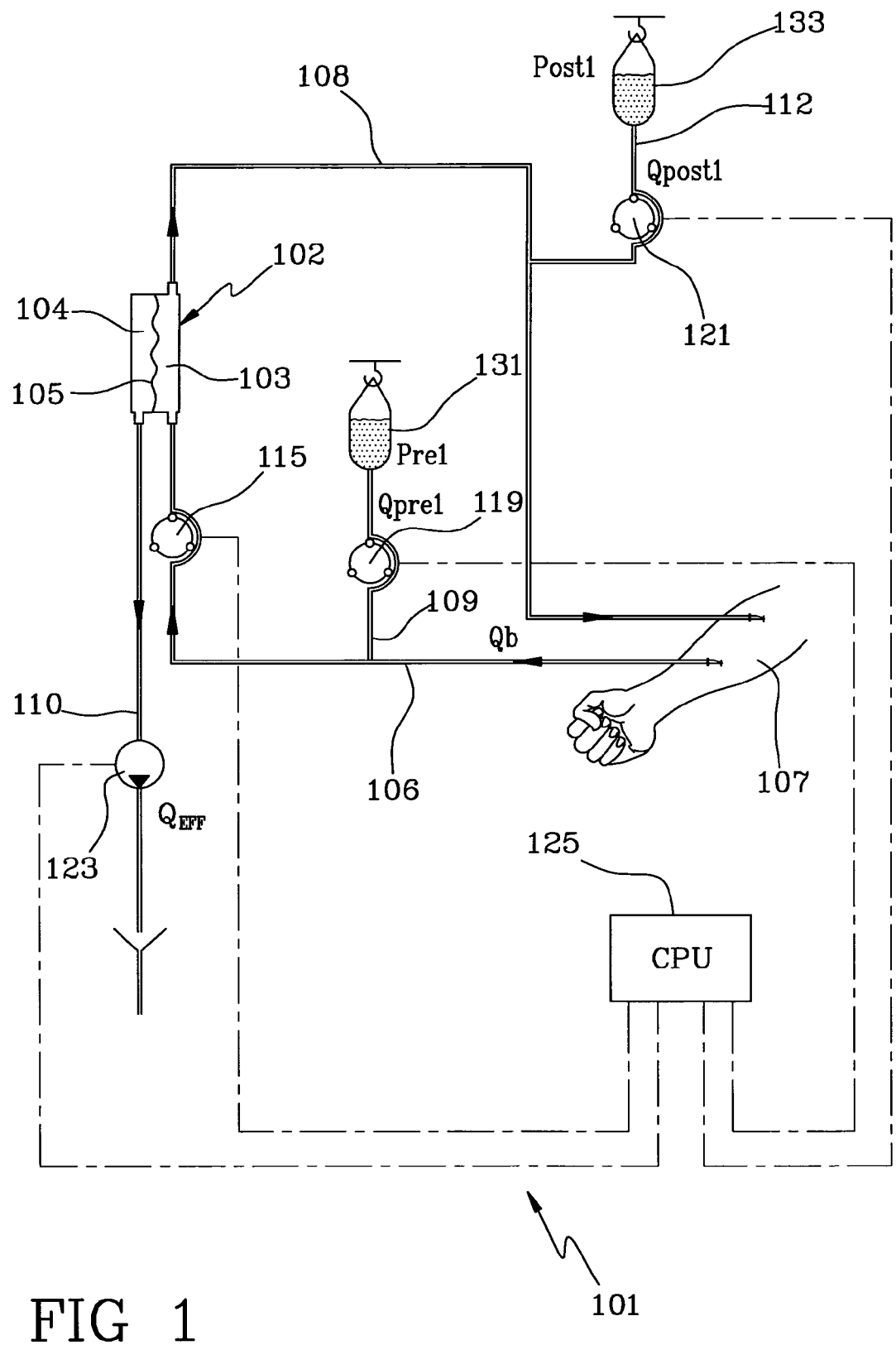
FIGS. 1, 1', 2, 3 and 4 illustrate hydraulic diagrams of the extracorporeal blood circuit used for the treatment, more particularly.
Figure 1:
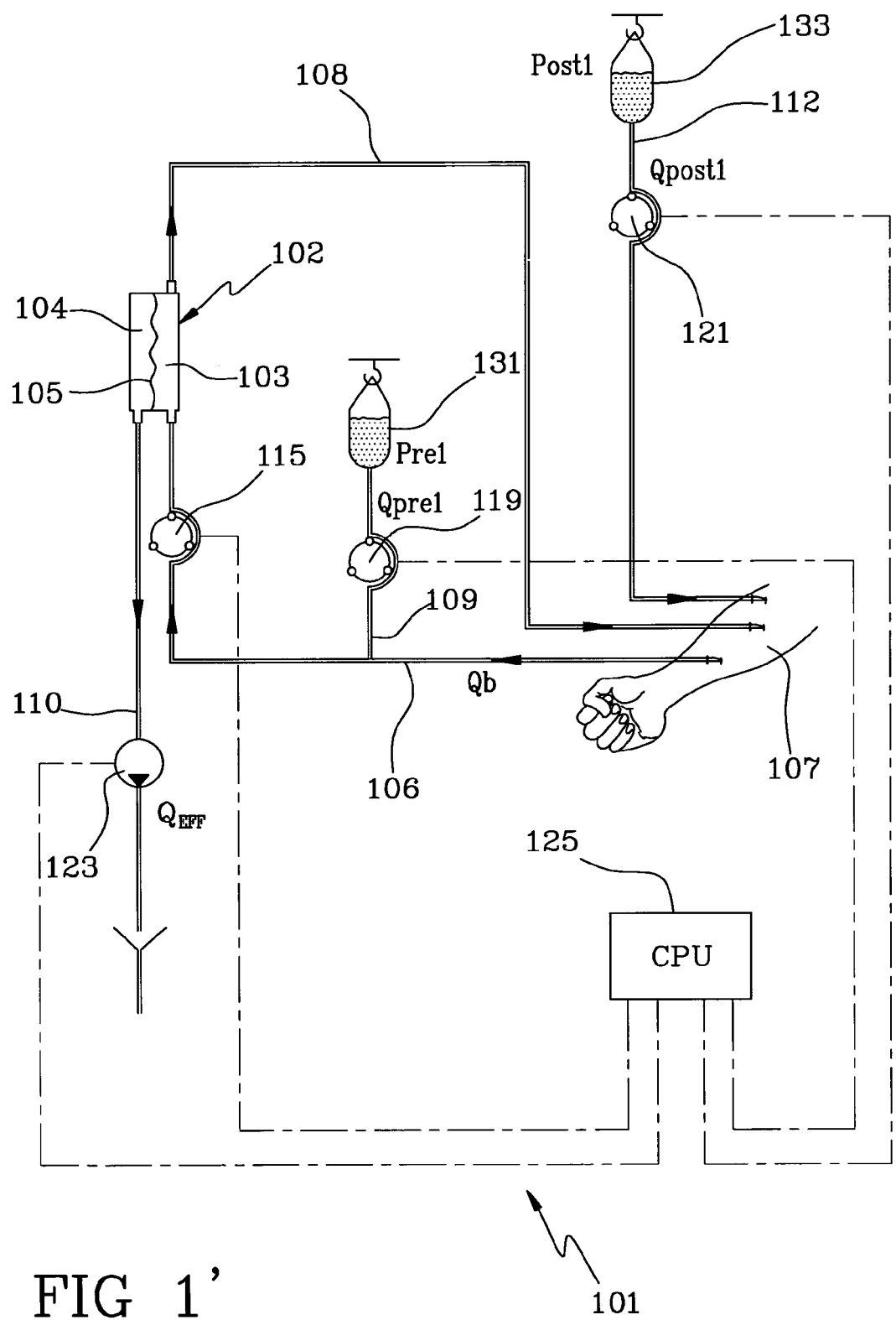
Figure 2:
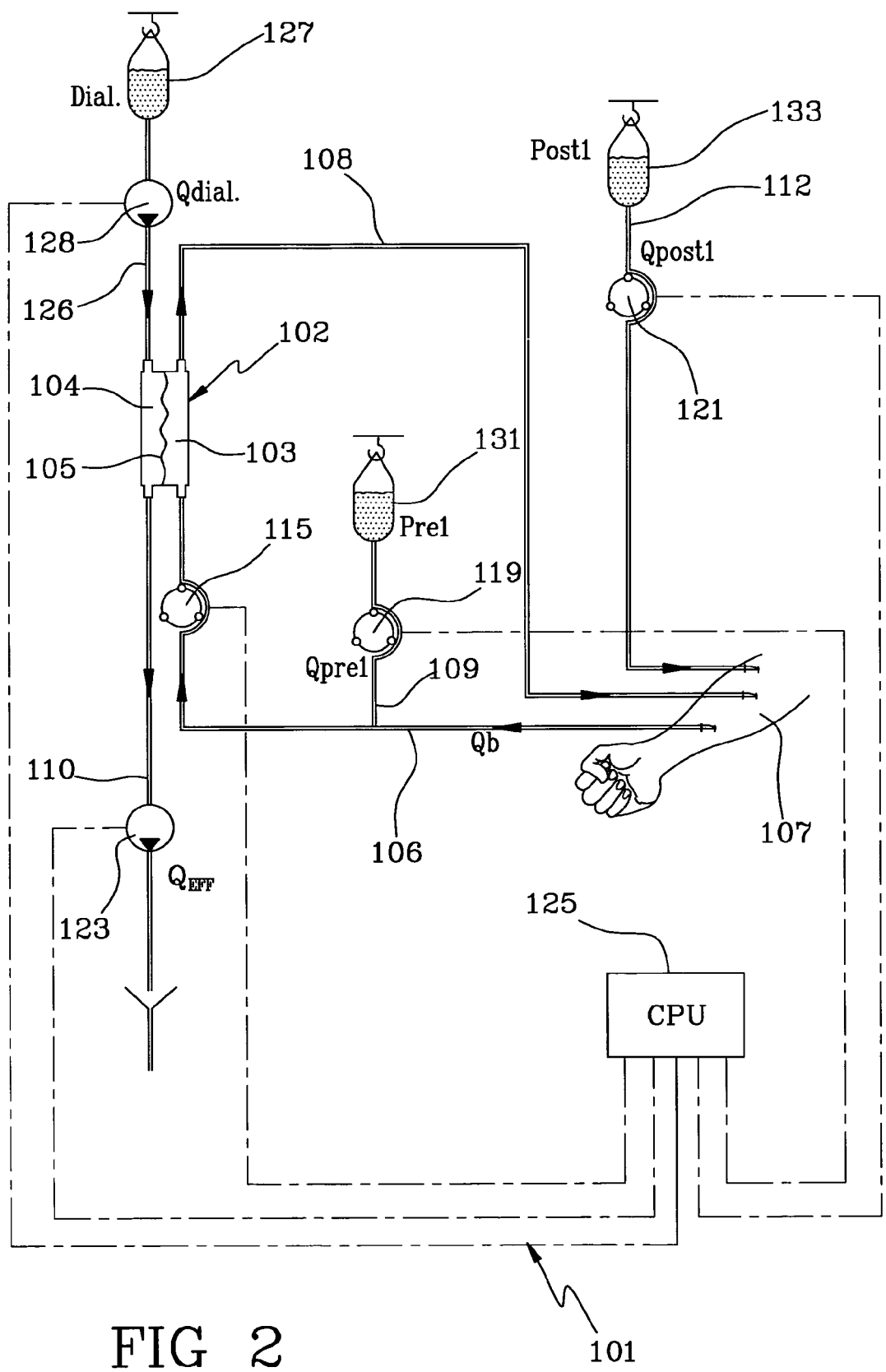
FIG. 2 represents the hydraulic diagram of the circuit for a CVVHD treatment mode by hemodialysis.
Figure 3:
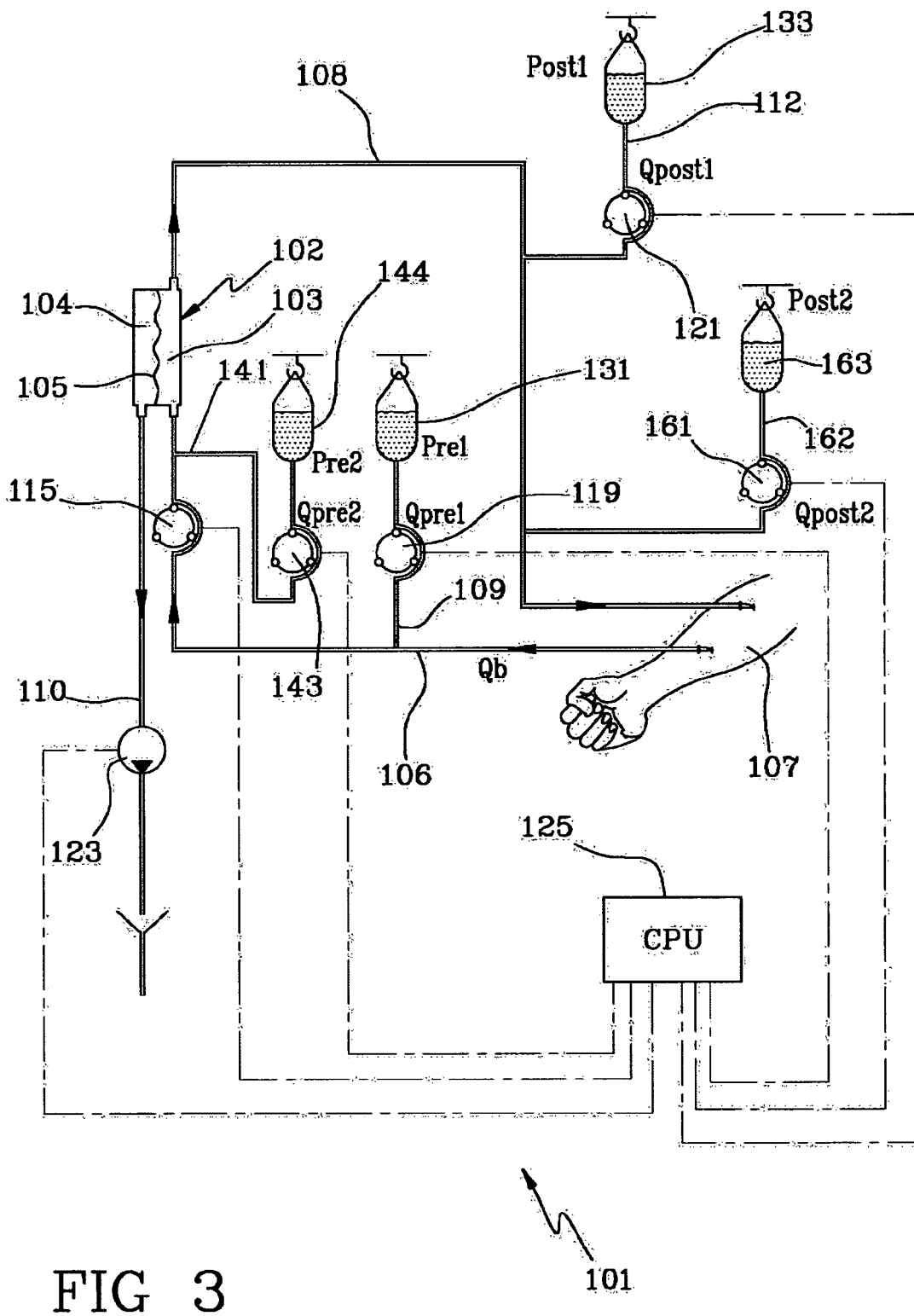
FIG. 3 represents the hydraulic diagram of the circuit for a CVVHF treatment mode by hemofiltration with replacement solution pre-infusion in addition to anticoagulation liquid solution pre-infusion, and with replacement solution post-infusion in addition to post-infusion of a solution for at least partially restoring the ionic balance.
Figure 4:
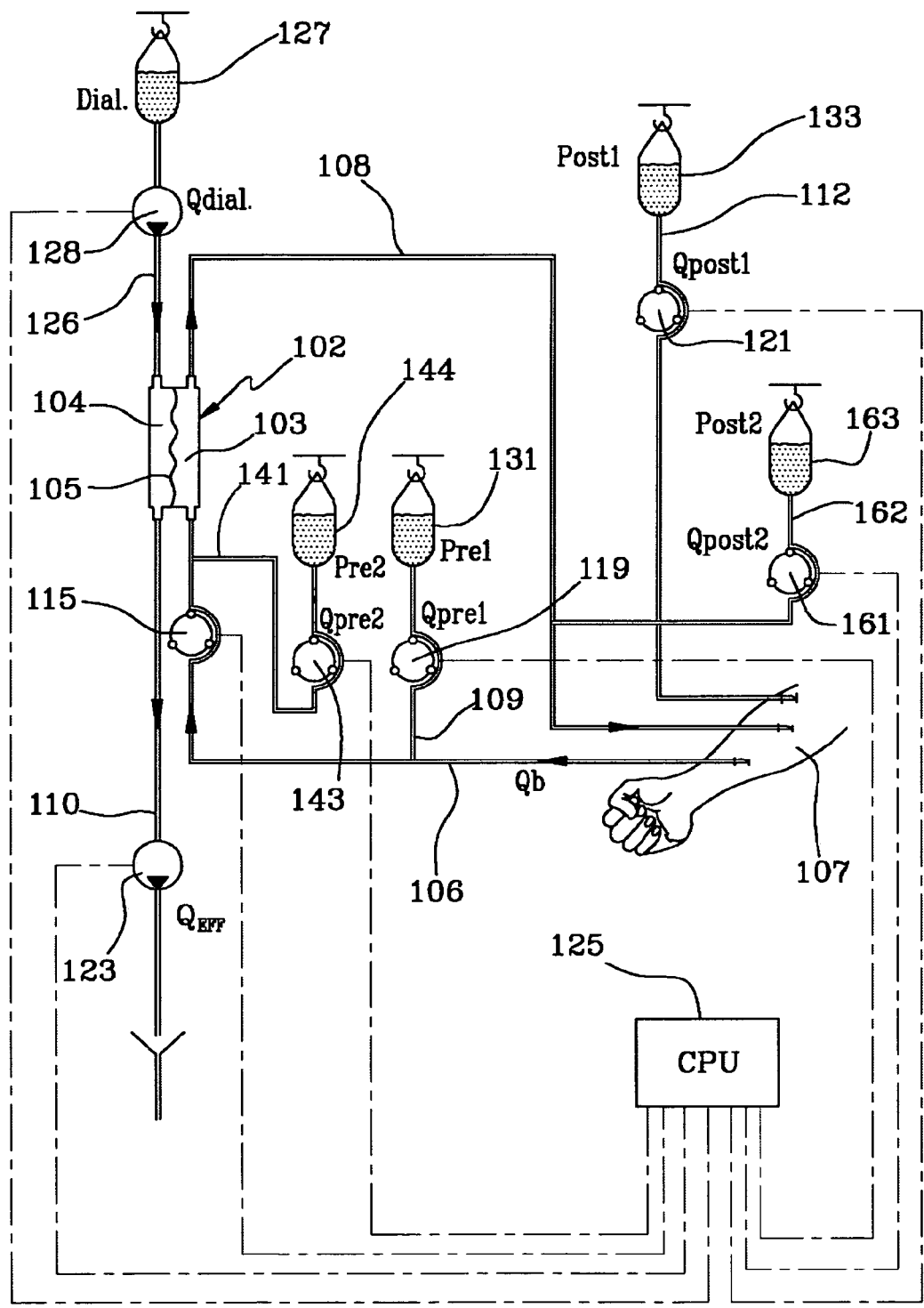
FIG. 4 represents the hydraulic diagram of the circuit for a CVVHDF treatment mode by hemodiafiltration with replacement solution pre-infusion in addition to anticoagulation liquid solution pre-infusion, and with replacement solution post-infusion in addition to post-infusion of a calcium solution for at least partially restoring the ionic balance.
Figure 5:
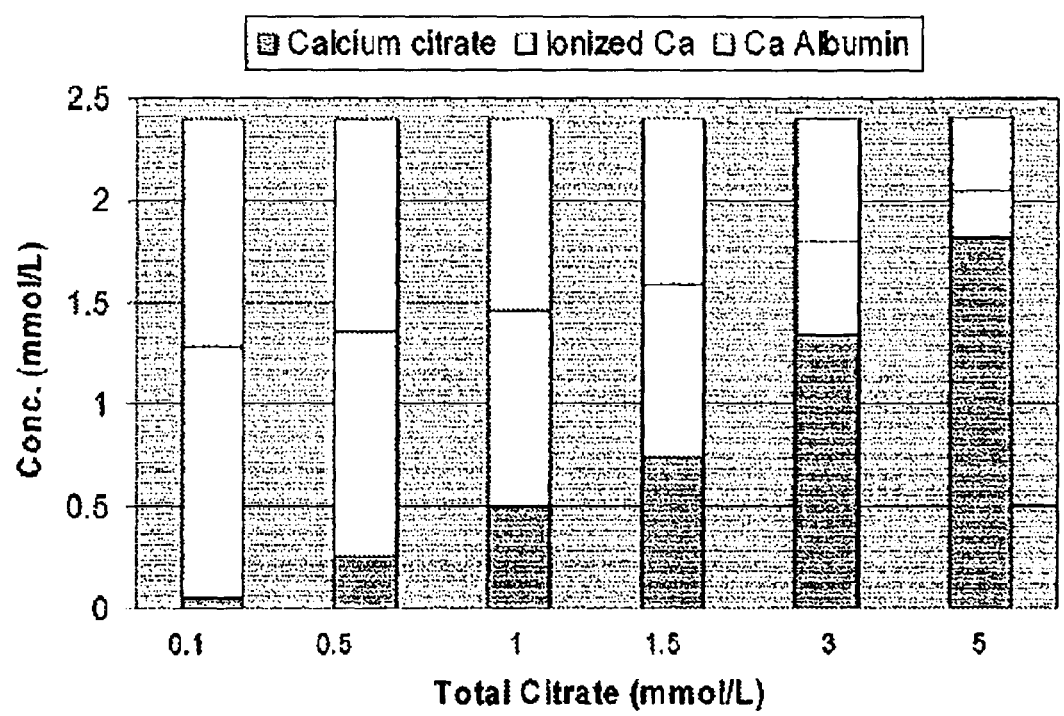

FIG. 5 is a Graph illustrating total citrate (mmoVL) as a function of concentration (mmoVL).

DETAILED DESCRIPTION OF THE INVENTION

The invention concerns a device for extracorporeal blood treatment 101 including:

a filter 102 having a primary 103 and a secondary 104 chamber separated by a semi-permeable membrane 105, a withdrawal line 106 connected to the primary chamber 103 of the filter 102, withdrawal line 106 operationally associated to a first means for regulating blood flow rate Qb 115, a return line 108 at the outlet of the primary chamber 103 of the filter 102, a first pre-infusion line 109 connected to a local anticoagulation substance container 131 and connected to withdrawal line 106, and operationally associated to a second means for regulating anticoagulation liquid flow rate Qpre1 119, a first post-infusion line 112 connected to a container of a solution at least partially restoring blood ionic balance 133 and connected directly to the patient (or to the return line) and operationally associated to a third means for regulating the ionic balance restoring solution flow rate Qpost1 121, an effluent line 110 connected at the outlet of the secondary chamber 104 of the filter 102, connected to a drain pipe and operationally associated to a fourth means for regulating effluent liquid flow rate Qeff 123, characterized in that it includes a CPU 125 including first means programmed to receive the signal output by at least one of the means for regulating liquid flow rate 115, 119, 121, 123 and second means programmed to control at least the third means for regulating the flow rate of the ionic balance restoring solution flow rate Qpost1 121 according to the input flow rate equal to the blood flow rate Qb, effluent liquid flow rate Qeff, and anticoagulation liquid flow rate Qpre1.

This control is valid for any type of treatment described including SCUF, CVVHD, CVVHF and CVVHDF.

The device according to the invention may include the second means of the CPU programmed in order to control at least the third means for regulating the ionic balance restoring solution flow rate Qpost1 according to the following equation (1):

$$Qpost1 = \alpha \times Fdilu \times K \qquad (1)$$

with $\alpha$ = constant, $A$ = constant, $$Fdilu = \frac{Qb}{(Qb + Qpre1)}, \text{ and}$$

$$K = A \times Qeff.$$

The device according to the invention may alternately include at least one of the four following elements:

a second pre-infusion line 141 connected to a source of a substance to be injected in the blood containing no local anticoagulation substance 144, said line being operationally associated to a fifth means for regulating pre-infusion replacement solution flow rate Qpre2 143, a second post-infusion line 162 connected to a second container of a solution particularly not permitting to restore at least partially the blood ionic balance 163, said second line being connected to the return line and a sixth means for regulating post-infusion replacement solution flow rate Qpost2 161, an input line 126 connecting a source of dialysis liquid 127 to the secondary chamber 104 of filter 102 and a seventh means for regulating dialysis liquid flow rate Qdial 128 operationally associated to said input line (the dialysis liquid solution particularly not permitting to restore at least partially the blood ionic balance, i.e. not containing calcium), additional CPU means 125 to control the fourth means for regulating effluent liquid flow rate Qeff 123 in order to produce a rate of desired weight loss or fluid removal flow rate Qwl of the patient.

In this case the first CPU means are programmed to receive the signal output by at least one of the fifth, sixth, seventh and fourth means for regulating liquid flow rate 143, 161, 128, 123, and the second CPU means are programmed to control at least the third means for regulating the ionic balance restoring solution flow rate Qpost1 121 as a function of the input flow rate equal to the blood flow rate Qb, the effluent liquid flow rate Qeff, the anticoagulation liquid flow rate Qpre1 and the at least one among the four following flow rates: pre-infusion replacement solution flow rate Qpre2, post-infusion replacement solution flow rate Qpost2, dialysis liquid flow rate Qdial and fluid removal flow rate Qwl.

This control works for all treatment modes having at least one of the following features: a second pre-injection, a second post-injection, a dialysis liquid, and a patient weight loss achieved by means for regulating the effluent flow rate.

In this mode, the device according to the invention may have its second CPU means programmed to control at least the third means for regulating the ionic balance restoring solution flow rate Qpost1 121 according to the equation:

$$Qpost1 = \alpha \times Fdilu \times K \quad (1)$$

with $\alpha$ = constant, $A$ = constant, $$Fdilu = \frac{Qb}{(Qb + Qpre1 + Qpre2)},$$

and $$K = A \times Qdial + Qpre1 + Qpre2 + Qpost2 + Qwl) \quad (2)$$

In this case, the liquid post-infusion at least partially restoring the ionic balance is not compensated in terms of volume.

Alternately, the device according to the invention may have its second CPU means programmed to control at least the third means for regulating the ionic balance restoring solution flow rate Qpost1 121 according to the equation:

$$Qpost1 = \alpha \times Fdilu \times K \quad (1)$$

With $\alpha$ = constant, $A$ = constant, $$Fdilu = \frac{Qb}{(Qb + Qpre1 + Qpre2)},$$

$$K = \frac{A}{1 - \alpha x A x Fdilu} \times (Qdial + Qpre1 + Qpre2 + Qpost1 + Qpost2 + Qwl)$$

In this case, the liquid post-infusion at least partially restoring the ionic balance is compensated in terms of volume.

Also the device according to the invention may have memory means included in its CPU and containing the value of A and where A is equal to 1.

Alternately, and to refine the calculation, the device where the CPU includes memory means containing the value of filter transmittance SC, and where A is equal to the filter transmittance SC, preferably the transmittance for transferable calcium. Filter transmittance SC (Sieving Coefficient) is defined as the ratio of the sum of the concentrations of the calcium species present in the effluent line and of the sum of the concentrations of the same species present in the diluted blood feeding the filter. Therefore this calculation considers the average transmittance for the various calcium species in question. Filter transmittance SC could range between 0 and 1.2.

Filter transmittance SC may be assumed equal to 1 because of the small size of transferable Ca species.

According to the invention, the device may have its CPU 125 with memory means containing the value of filter 102 parameter K0xS, K0xS being the product of the filter transfer coefficient K0 and the filter exchange surface S, and its CPU 125 second means programmed to control at least the third means for regulating the ionic balance restoring solution flow rate Qpost1 121 according to the input flow rate equal to the blood flow rate Qb, anticoagulation liquid flow rate Qpre1, pre-infusion replacement solution flow rate Qpre2, effluent liquid flow rate Qeff, and parameter K0xS.

In this case, the treatment modes HD and HDF are especially targeted.

The filter transfer coefficient or coefficient K0 is determined for the calcium species transferred preferably in CVVHD mode.

More in detail, and in a particular case wherein Qeff=Qb, the device may have its CPU 125 second means programmed to control at least the third means for regulating the ionic balance restoring solution flow rate Qpost1 121 according to the following equation:

$$Qpost1 = \alpha \times Fdilu \times K \quad (1)$$

with $\alpha$ = constant, $$Fdilu = \frac{Qb}{(Qb + Qpre1 + Qpre2)}$$

$$K = Qb \times \frac{NT}{(1+NT)}, \text{ and } NT = K0 \times S / Qb.$$

Where NT is the ratio between filter transfer (filter parameter) and the blood flow, K0 is the filter transfer coefficient and S is the filter exchange surface area. Alternately, in another particular case, the device according to the invention may have its CPU 125 second means programmed to control at least the third means for regulating the ionic balance restoring solution flow rate Qpost1 121 according to the following equation:

$$Qpost1 = \alpha \times Fdilu \times K \quad (1)$$

With $\alpha$ = constant, $$Fdilu = \frac{Qb}{(Qb + Qpre1 + Qpre2)}$$

$$K = Qb \times \frac{(e-1)}{(e-Z)} \text{ with } Z \text{ different from } 1$$

$$E = \exp(NT \times (1-Z)),$$

$$Z = \frac{Qb}{Qeff}$$

$$NT = Ko \times S / Qb$$

This mode of clearance approximation is advantageous in CVVHD and CVVHDF treatments. It is to be noted that the above equations are relevant to counter-current blood/dialysis liquid flow and those skilled in the art may easily develop similar equations for the co-current case.

On the other hand the device according to the invention may comprise at least one of the two following elements:
- a second pre-infusion line 141 connected to the source of a substance to be injected in the blood and not containing a local anticoagulation substance 144, the said line being operationally associated to a fifth means for regulating pre-infusion replacement solution flow rate Qpre2 143,
- an input line 126 connecting the source of dialysis liquid 127 to the secondary chamber 104 of filter 102 and a seventh means for regulating dialysis liquid flow rate Qdial 128 operationally associated to the said input line.

In this case, the CPU 125 includes memory means containing the value of filter parameter K0xS, K0xS being the product of filter transfer coefficient K0 and filter exchange surface area S, and where CPU 125 second means are programmed to control at least the third means for regulating the ionic balance restoring solution flow rate Qpost1 121 according to the input flow rate equal to the blood flow rate Qb, anticoagulation liquid flow rate Qpre1, and at least one of the following flow rates: pre-infusion replacement solution flow rate Qpre2, effluent liquid flow rate Qeff, dialysis liquid flow rate Qdial and parameter K0xS. Here, fresh dialysis liquid is present.

In particular in this case, the device may have its CPU 125 second means programmed to control at least the third means for regulating the ionic balance restoring solution flow rate Qpost1 121 according to the following equation:

$$Qpost1 = \alpha \times Fdilu \times K \qquad (1)$$

With $\alpha$ = constant, $$Fdilu = \frac{Qb}{(Qb + Qpre1 + Qpre2)}$$

$$K = Qb \times \frac{(e-1)}{(e-Z)} \text{ with } Z \text{ different from } 1$$

$$E = \exp(NT \times (1-Z)),$$

$$Z = \frac{Qb}{Qdial},$$

$$NT = K0 \times S / Qb$$

$$K = Kd \times (1 - (Qeff - Qdial)/Qb) + (Qeff - Qdial),$$

Where $Z$ is the ratio beween blood flow rate and dialysis liquid flow rate, $K$ is a flow parameter and $Kd$ is a reference flow parameter.

Where Z is the ration between blood flow rate and dialysis liquid flow rate, k is a flow parameter and Kd is a reference flow parameter.

Alternately to what has just been described, the device may have its CPU 125 second means programmed to control at least the third means for regulating the ionic balance restoring solution flow rate Qpost1 121 according to the following equation:

$$Qpost1 = \alpha \times Fdilu \times K \qquad (1)$$

With $\alpha$ = constant,

-continued $$Fdilu = \frac{Qb}{(Qb + Qpre1 + Qpre2)}$$

$$K = \frac{Qb \times Qdial - f \times (Qb - (Qeff - Qdial)) \times Qeff}{Qdial - f \times (Qb - (Qeff - Qdial))}$$

with $f = \left[\frac{Qb - (Qeff - Qdial)}{Qb} \times \frac{Qeff}{Qdial}\right]^{t/\gamma}$ $\gamma = \exp((Qeff - Qdial)/K0 \times S) - 1$ In any case, the device according to the invention may have the local anticoagulation solution containing citrate ions, and the solution for at least partially restoring the ionic balance containing calcium ions.

In any case, the device according to the invention may have CPU 125 including means to memorize at least a value chosen among one of the following values:
- First value: $\alpha$ is a constant within the interval [0.002; 0.01]; this value may be considered for a calcium injection with concentrated calcium solutions. For example it could be about calcium solutions with CaCl2 and Ca gluconate.
- Second value: $\alpha$ is a constant within the interval [0.001; 0.2]: upper range of this second value may be considered for a diluted calcium solution injection around 10 mmol/L (10 mmol/L when a is close to 0.15-0.20).

In any case, since the device operates with citrate ions and calcium ions, it may have CPU 125 including means to memorize at least another (third) value $\alpha=\beta\times[CaTot]/[CaPost1]$ (10) where
- $\beta$ is a constant (and it is the same as FRACTION) within the interval [0.3; 1];
- [CaTOT] is the total concentration of blood calcium withdrawn from the patient;
- [CaPost1] is the calcium concentration of the solution at least partially restoring the ionic balance of the blood.

In fact, $\beta^*[CaTOT]$ is the calcium concentration that may be transferred through the semi-permeable membrane. The calcium species that may be transferred through the membrane comprise mainly ionized calcium as well as calcium-citrate and calcium bicarbonate complexes of small molecular mass (for example of molecular mass <500 g/mole, as explained above. Preferably CaTot ranges between [1.8 mmol/L; 2.4 mmol/L], corresponding to the patient's physiological state, the preferred value being equal to 2.2. In some cases of hepatic patients, the upper value may reach 4.

CPU 125 may include means to memorize at least the $\beta$ value within the range [0.80; 1]. The $\beta$ value is preferably equal to 0.95. $(1-\beta)\times CaTOT$ represents the fraction of the total remaining protein-bound calcium and $\beta\times CaTOT$ represents all the species transferable through the filter. $\beta$ is modulated by the blood composition (hematocrit, proteins, bicarbonates, Mg, pH) and by the quantity of citrate. The usual citrate anticoagulation parameters are meant to establish a concentration in ionized calcium around 0.3-0.4 mmol/L at the outlet of the filter. Under such conditions, the fraction of protein-bound calcium is strongly decreased and in the order of 5% of total calcium. This is why a $\beta$ value=0.95 is considered by default.

According to the invention, the CPU may include:
memory means to memorize at least the value $$\alpha=\beta\times[CaTot]/[CaPost1] \qquad (10),$$

memory means containing a chemical balance modeling algorithm in the hydraulic circuit of the extracorporeal treatment, and means, in the beginning of the treatment or several times during the treatment, to calculate by model, a value of parameter β as a function of measured values or by default of: the patient's hematocrit Hct, the total protein (albumin) concentration Cp in the patient's blood, HCO3 concentration, the patient's total Ca concentration [CaTot], possibly the total magnesium concentration, concentration of citrate in the circuit after its injection or systemic.

For the model, a software package exists using notably Newton Rapson's resolution method.

The device according to the invention may have CPU 125 with memory means containing a memorized value of the patient's hematocrit Hct, and where the entering flow rate is equal to Qbx(1−Hct). Such input flow rate is refined and represents the plasma flow rate. Hct value may alternately be entered by the user via an interface connected to the device and in communication with CPU 125. By default the Hct value may be set equal to 0.30.

Alternatively and in a more refined way, the device according to the invention may have CPU 125 with memory means containing a memorized value of the patient's hematocrit Hct and a value Cp of the total concentration in proteins in the blood, where the entering blood flow rate is equal to Qb×(1−Hct)×(1−μ); where μ is the volumetric fraction occupied by the proteins in the patient's blood and equals to Cp/1000. The input flow rate is refined here to the flow rate of plasmatic water. Hct and Cp may be entered alternatively by the user via an interface connected to the device and in communication with CPU 125.

In particular the preferred embodiment requests the user to enter the hematocrit value only.

By default, value Cp may be set at 50 g/l.

In all modes of the invention, other features of the invention are the following:
 the dialysis liquid may include no calcium ions,
 every means for regulating each of the described liquid flow rates may include a pump or a valve,
 every means for measuring each of the described liquid flow rates may include a flow meter or a scale,
 the regional anticoagulation solution contains citrate ions,
 the regional anticoagulation solution contains a solution of trisodium citrate;
 the regional anticoagulation solution contains a citrate and citric acid solution; more specifically it may be an Anticoagulant Citrate Dextrose (ACD) solution with trisodium citrate and monohydrated citric acid,
 the solution at least partially restoring the ionic balance of the blood contains calcium ions,
 the solution at least partially restoring the ionic balance of the blood may contain an isotonic solution, e.g. calcium chloride and magnesium chloride.

The first pre-infusion line is, in one embodiment of the invention, connected to the withdrawal line upstream of the first means for regulating the blood flow rate Qb, and the second pre-infusion line is connected to the withdrawal line downstream of the first means for regulating the blood flow rate Qb.

Also the device according to the invention providing several modes of treatment—HD, HDF, UF, HF, each mode with or without pre-dilution, each mode with or without post-dilution
 may include at least a scale to weigh a closed liquid reservoir if necessary, for example a reservoir for pre-infusion 1, a reservoir for pre-infusion 2, a reservoir for dialysis liquid (fresh), a reservoir for effluent, a reservoir for post-infusion liquid 1, a reservoir for post-infusion liquid 2. The scales may weigh a reservoir individually or the sum of several reservoirs. The CPU has some means to receive signal output by at least one of the scales and means to control one or several means for regulating the liquid flow rate according to the signal output by at least one of the scales.

The invention also concerns the procedure for extracorporeal blood treatment in a blood treatment device 101 containing:
 a filter 102 having a primary 103 and a secondary 104 chamber separated by a semi-permeable membrane 105,
 an withdrawal line 106 connected to primary chamber 103 of filter 102,
 withdrawal line 106 is operationally associated to a first means for regulating blood flow rate Qb 115,
 a return line 108 at the outlet of the primary chamber 103 of filter 102,
 a first pre-infusion line 109 connected to a local anticoagulation substance container and connected to the withdrawal line 106, and operationally associated to a second means for regulating anticoagulation liquid flow rate Qpre1 119,
 a first post-infusion line 112 connected to a container of a solution at least partially restoring the ionic balance of the blood, and connected to the return line and operationally associated to a third means for regulating the ionic balance restoring solution flow rate Qpost1 121,
 an effluent line 110 connected at the outlet of the secondary chamber 104 of filter 102, connected to a drain pipe and operationally associated to a fourth means for regulating liquid effluent liquid flow rate Qeff 123,
 a CPU 125 to receive signal from at least one of the means for regulating the flow rate and to control at least one means for regulating the flow rate, the procedure including the following steps:
 a) receiving signal output by at least one of the means for regulating liquid flow rate 115, 119, 123, and
 b) controlling at least the third means for regulating the ionic balance restoring solution flow rate Qpost1 121 as a function of the blood flow rate Qb, effluent liquid flow rate Qeff and anticoagulation liquid flow rate Qpre1.

All features described applying to the device may be transferred by analogy to the procedure by those skilled in the art and are included in this description.

The invention, in an alternative, relates to a device for blood treatment (by extracorporeal circulation) 101 including:
 a filter 102 having a primary 103 and a secondary 104 chamber separated by a semi-permeable membrane 105,
 an withdrawal line 106 connected to the primary chamber 103 of filter 102,
 the withdrawal line 106 is operationally associated to a first means for regulating blood flow rate Qb 115,
 a return line 108 at the outlet of the primary chamber 103 of filter 102,
 a first pre-infusion line 109 connected to a local anticoagulation substance container 131 and connected to the withdrawal line 106, and operationally associated to a second means for regulating anticoagulation liquid flow rate Qpre1 119,
 a first post-infusion line 112 connected to a container of a solution at least partially restoring blood ionic balance 133 and connected to the return line, and operationally associated to a third means for regulating the ionic balance restoring solution flow rate Qpost1 121,
 an effluent line 110 connected at the outlet of the secondary chamber 104 of filter 102, connected to a drain pipe and operationally associated to a fourth means for regulating liquid effluent liquid flow rate Qeff 123,
a CPU 125 including:
  first means programmed to receive signal output by at least one of the means for regulating liquid flow rate 115, 119, 121, 123,
  third means to calculate by simulation the concentrations of calcium under different forms so as to calculate afterwards the number FRACTION,
  possibly further means to calculate Ca Clearance as a function, for example, of flow rates and filter characteristics (K0xS),
  fourth means programmed to control at least the third means for regulating the ionic balance restoring solution flow rate Qpost1 121 according to [CaTot], FRACTION and Ca Clearance as already defined in the previous text.

For example the control may occur according to the previously defined equation A hereinafter reported:

$$Q\text{post1} = [\text{CaTot}] \times \text{FRACTION} \times \text{Ca Clearance} / [\text{CaPost1}],$$

Or according to the previously defined equation A' hereinafter reported where the clearance is approximated:

$$Q\text{post1} = [\text{CaTot}] \times \text{FRACTION} \times Qb/(Qb+Q\text{pre}) \times Qeff / [\text{CaPost1}]$$

In this alternative, the procedure would be a procedure of blood treatment by extracorporeal circulation in a blood treatment device 101 including:
  a filter 102 having a primary 103 and a secondary 104 chamber separated by a semi-permeable membrane 105,
  an withdrawal line 106 connected to the primary chamber 103 of filter 102,
  the withdrawal line 106 is operationally associated to a first means for regulating blood flow rate Qb 115,
  a return line 108 at the outlet of the primary chamber 103 of filter 102,
  a first pre-infusion line 109 connected to a local anticoagulation substance container and connected to the withdrawal line 106, and operationally associated to a second means for regulating anticoagulation liquid flow rate Qpre1 119,
  a first post-infusion line 112 connected to a container of a solution at least partially restoring the ionic balance of the blood, and connected to the return line and operationally associated to a third means for regulating the ionic balance restoring solution flow rate Qpost1 121,
  an effluent line 110 connected at the outlet of the secondary chamber 104 of filter 102, connected to a drain pipe and operationally associated to a fourth means for regulating liquid effluent liquid flow rate Qeff 123,
  a CPU 125 to receive signal from at least one of the means for regulating the flow rate and to control at least one means for regulating the flow rate, the procedure including the following steps:

a) receiving signal output by at least one of the means for regulating liquid flow rate 115, 119, 123,
b) calculating by simulation the concentrations of different calcium species,
c) calculating the number FRACTION from the concentrations calculated by simulation,
d) possibly calculating Ca Clearance as a function, for example, of flow rates and filter characteristics (K0xS),
e) controlling at least the third means for regulating the ionic balance restoring solution flow rate Qpost1 121 according to [CaTot], FRACTION and Ca Clearance.

For example the control may occur according to the following equation A:

$$Q\text{post1} = [\text{CaTot}] \times \text{FRACTION} \times \text{Clearance Ca} / [\text{CaPost1}],$$

Or according to the following equation A' where the clearance is approximated:

$$Q\text{post1} = [\text{CaTot}] \times \text{FRACTION} \times Qb/(Qb+Q\text{pre}) \times Qeff / [\text{CaPost1}]$$

It is also to be noted that it is possible to infuse C×estimated Ca Loss,
where C is an operator set coefficient (constant) which default value is 1.0 and aims at controlling the calcium balance:
  C>1 is used to infuse more calcium than the computed loss=>positive net calcium balance expected
  C<1 is used to infuse less calcium than the computed loss=>negative net calcium balance expected C might be called 'calcium compensation' and might be part of the medical prescription; typically C is comprised between 0 and 3.

In term of alpha definition the previously mentioned equation 10 will be modified as follows:

$$\alpha = C \times \beta \times [\text{CaTOT}] / [\text{CaPost1}].$$

Advantages of the Invention
  the invention enables a precise control of the flow rate of a solution restoring ionic balance during a treatment session;
  the invention enables an adaptable control of the flow rate of a solution restoring ionic balance during a treatment session;
  the invention enables a control of the flow rate of a solution restoring ionic balance in the same machine offering several methods of blood treatment as stated above: ultrafiltration, hemodialysis, hemofiltration, hemodiafiltration, and those with or without pre-dilution replacement solution, with or without post-dilution replacement solution;
  the invention enables a control of the flow rate of a solution restoring "free" ionic balance, i.e. possible according to a wide range of concentrations of the initial solution of regional anticoagulation, and notably enables the use of a physiological regional anticoagulation solution, e.g. the solution PRISMOCITRATE marketed by GAMBRO avoiding patient hypernatraemia problems.

The invention claimed is:
1. Device for extracorporeal blood treatment comprising:
  a filter having a primary and a secondary chamber separated by a semi-permeable membrane,
  a withdrawal line connected to the primary chamber of the filter,
  the withdrawal line operationally associated to a first means for regulating blood flow rate Qb,
  a return line at the outlet of the primary chamber of the filter,
  a first pre-infusion line connected to a local anticoagulation substance container and connected to the withdrawal line, and operationally associated to a second means for regulating anticoagulation liquid flow rate Qpre1,
  a first post-infusion line connected to a container of a solution at least partially restoring blood ionic balance for infusing the solution in the blood and operationally associated to a third means for regulating the ionic balance restoring solution flow rate Qpost1,
  an effluent line connected at the outlet of the secondary chamber of filter, connected to a drain pipe and opera- tionally associated to a fourth means for regulating liquid effluent liquid flow rate Qeff, wherein the device includes a CPU including a first module programmed to receive the signal output by at least one of the first, second, third and fourth means for regulating liquid flow rate and second module programmed to control at least the third means for regulating the ionic balance restoring solution flow rate Qpost1 as a function of the input flow rate equal to and chosen in the group consisting of blood flow rate Qb, plasma water blood flow rate $Q_{pw}$, plasma flow rate $Q_p$, effluent liquid flow rate Qeff and anticoagulation liquid flow rate Qpre1, wherein CPU second module is programmed to control at least the third means for regulating the ionic balance restoring solution flow rate Qpost1 as a function of the following equation (1):

$$Qpost1 = \alpha \times Fdilu \times K \quad (1)$$

with:

$\alpha$ = constant, $A$ = constant, $$Fdilu = \frac{Qb}{(Qb + Qpre1)}, \text{ or } Fdilu = \frac{Qpw}{(Qpw + Qpre1)}, \text{ or}$$

$$Fdilu = \frac{Qp}{(Qp + Qpre1)}$$

$K = A \times Qeff$,

Qpw being the plasma water flow rate,

Qp being the plasma flow rate,

Fdilu being the dilution ratio,

K being a flow parameter comprising the product of a constant and the effluent liquid flow rate.

2. Device according to claim 1 comprising at least one element chosen in the group consisting of:
  a second pre-infusion line connected to a source of a substance to be injected in the blood containing no local anticoagulation substance, said line being operationally associated to a fifth means for regulating pre-infusion replacement solution flow rate Qpre2,
  a second post-infusion line connected to a second container of a solution, said second line being connected to the return line and to a sixth means for regulating post-infusion replacement solution flow rate Qpost2,
  an input line connecting a source of dialysis liquid to the secondary chamber of filter and a seventh means for regulating dialysis liquid flow rate Qdial operationally associated to said input line,
  an additional CPU module to control the fourth means for regulating effluent liquid flow rate Qeff to produce a rate of desired weight loss of the patient or fluid removal flow rate Qwl,
  the CPU first module is programmed to receive signal output by at least one means chosen in the group consisting of the fifth means, sixth means, seventh means and fourth means for regulating liquid flow rate,
  the CPU second module is programmed to control at least the third means for regulating the ionic balance restoring solution flow rate Qpost1 as a function of the input flow rate equal to Qb, effluent liquid flow rate Qeff, anticoagulation liquid flow rate Qpre1, and at least one flow rate chosen in the group consisting of: pre-infusion replacement solution flow rate Qpre2, post-infusion replacement solution flow rate Qpost2, dialysis liquid flow rate Qdial and fluid removal flow rate Qwl.

3. Device according to claim 2, wherein the CPU second module is programmed to control at least the third means for regulating the ionic balance restoring solution flow rate Qpost1 according to the equation:

$$Qpost1 = \alpha \times Fdilu \times K \quad (1)$$

with:

$\alpha$ = constant, $A$ = constant, $$Fdilu = \frac{Qb}{(Qb + Qpre1 + Qpre2)}, \text{ or}$$

$$Fdilu = \frac{Qpw}{(Qpw + Qpre1 + Qpre2)}, \text{ or}$$

$$Fdilu = \frac{Qp}{(Qp + Qpre1 + Qpre2)}$$

$$K = A \times (Qdial + Qpre1 + Qpre2 + Qpost2 + Qwl) \quad (2)$$

Qpw being the plasma water flow rate,

Qp being the plasma flow rate,

Fdilu being the dilution ratio,

K being a flow parameter.

4. Device according to claim 2, wherein the CPU second module is programmed to control at least the third means for regulating the ionic balance restoring solution flow rate Qpost1 according to the equation:

$$Qpost1 = \alpha \times Fdilu \times K \quad (1)$$

with $\alpha$ = constant, $A$ = constant, $$Fdilu = \frac{Qb}{(Qb + Qpre1 + Qpre2)}, \text{ or}$$

$$Fdilu = \frac{Qpw}{(Qpw + Qpre1 + Qpre2)}, \text{ or}$$

$$Fdilu = \frac{Qp}{(Qp + Qpre1 + Qpre2)}$$

$$K = \frac{A}{1 - \alpha \times A \times Fdilu} \times (Qdial + Qpre1 + Qpre2 + Qpost1 + Qpost2 + Qwl);$$

Qpw being the plasma water flow rate,

Qp being the plasma flow rate,

Fdilu being the dilution ratio,

K being a flow parameter.

5. Device according to claim 1, wherein the CPU includes a memory containing the value A, and where A is equal to 1.

6. Device according to claim 1, wherein the CPU includes a memory containing filter transmittance value SC and where A is equal to filter transmittance SC.

7. Device according to claim 1, wherein the CPU includes a memory containing the value of parameter K0xS of filter, K0xS being the product of the filter transfer coefficient K0 and the effective filter exchange surface S, and wherein CPU second module is programmed to control at least the third means for regulating the ionic balance restoring solution flow rate Qpost1 as a function of input flow rate equal to blood flow rate Qb, anticoagulation liquid flow rate Qpre1, pre-infusion replacement solution flow rate Qpre2, effluent liquid flow rate Qeff and parameter K0xS.

8. Device according to claim 7, wherein CPU second module is programmed to control at least the third means for regulating the ionic balance restoring solution flow rate Qpost1 according to the following equation:

$$Qpost1 = \alpha \times Fdilu \times K \qquad (1)$$

With $\alpha$ = constant, $$Fdilu = \frac{Qb}{(Qb + Qpre1 + Qpre2)}, \text{ or}$$

$$Fdilu = \frac{Qpw}{(Qpw + Qpre1 + Qpre2)}, \text{ or}$$

$$Fdilu = \frac{Qp}{(Qp + Qpre1 + Qpre2)}$$

$$K = Qb \times \frac{(e-1)}{(e-Z)} \text{ with } Z \text{ different from } 1$$

$$E = \exp(NT \times (1 - Z)),$$

$$Z = \frac{Qb}{Qeff},$$

$$NT = K0 \times S / Qb,$$

Qp being the plasma flow rate,

Fdilu being the dilution ratio,

K being a flow parameter,

Z being a ratio between blood flow rate and effluent liquid flow rate,

Qpw and Qp being alternatively used instead of Qb in the K, NT and Z formulas.

9. Device according to claim 1, comprising following elements:
a second pre-infusion line connected to a source of a substance to be injected in the blood containing no local anticoagulation substance, said line being operationally associated to a fifth means for regulating pre-infusion replacement solution flow rate Qpre2,
an input line connecting a source of dialysis liquid to secondary chamber of filter, and a seventh means for regulating dialysis liquid flow rate Qdial operationally associated to said input line,
and wherein the CPU includes a memory containing the value of a parameter K0xS of the filter, K0S being the product of a filter transfer coefficient K0 and a filter effective exchange surface area S, and wherein CPU second module is programmed to control at least the third means for regulating the ionic balance restoring solution flow rate Qpost1 as a function of the input flow rate equal to Qb, anticoagulation liquid flow rate Qpre1, and at least one of the flow rates chosen in the group consisting of: pre-infusion replacement solution flow rate Qpre2, effluent liquid flow rate Qeff, dialysis liquid flow rate Qdial and the K0S parameter.

10. Device according to claim 9, wherein CPU second module is programmed to control at least the third means for regulating the ionic balance restoring solution flow rate Qpost1 according to the following equation:

$$Qpost1 = \alpha \times Fdilu \times K \qquad (1)$$

With $\alpha$ = constant, $$Fdilu = \frac{Qb}{(Qb + Qpre1 + Qpre2)}, \text{ or}$$

$$Fdilu = \frac{Qpw}{(Qpw + Qpre1 + Qpre2)}, \text{ or}$$

$$Fdilu = \frac{Qp}{(Qp + Qpre1 + Qpre2)}$$

$$Kd = Qb \times \frac{(e-1)}{(e-Z)} \text{ with } Z \text{ different from } 1$$

$$E = \exp(NT \times (1 - Z)),$$

$$Z = \frac{Qb}{Qdial},$$

$$NT = K0 \times S / Qb,$$

$$K = Kd \times (1 - (Qeff - Qdial) / Qb) + (Qeff - Qdial),$$

Qpw being the plasma water flux,

Qp being the plasma flux,

Fdilu being the dilution ratio,

Qpw and Qp being possibly used instead of Qb in the Kd, NT, K and f formulas.

11. Device according to claim 9, wherein CPU second module is programmed to control at least the third means for regulating the ionic balance restoring solution flow rate Qpost1 according to the following equation:

$$Qpost1 = \alpha \times Fdilu \times K \qquad (1)$$

With $\alpha$ = constant, $$Fdilu = \frac{Qb}{(Qb + Qpre1 + Qpre2)}$$

$$K = \frac{Qb \times Qdial - f \times (Qb - (Qeff - Qdial)) \times Qeff}{Qdial - f \times (Qb - (Qeff - Qdial))}$$

With $f = \left[ \frac{Qb - (Qeff - Qdial)}{Qb} \times \frac{Qeff}{Qdial} \right]^{t/y}$, $y = \exp((Qeff - Qdial)/(K0 \times S)) - 1$, Qpw being the plasma water flux, Qp being the plasma flux, Fdilu being the dilution ratio, Qpw and Qp being alternatively used instead of Qb in the Fdilu, K and f formulas.

12. Device according to claim 1, wherein the local anticoagulation solution contains citrate ions, and the solution for at least partially restoring the ionic balance contains calcium ions.

13. Device according to claim 1, wherein the CPU includes a module to memorize at least value a chosen among one of the following values:

First value: α is a constant within the interval 0.002 to 0.01;
Second value: α is a constant within the interval 0.001 to 0.2.

14. Device according to claim 12, wherein the CPU includes a module to memorize at least the value $$\alpha = C \times \beta \times [CaTOT]/[CaPost1] \quad (10)$$ where C is a constant coefficient set by the operator;
β is a constant within the range 0.3 to 1;
[CaTOT] is the total concentration of blood calcium withdrawn from the patient;
[CaPost1] is the calcium concentration of the solution at least partially restoring the ionic balance of the blood.

15. Device according to claim 14, wherein CPU includes a module to memorize at least value β within the range 0.80 to 1.

16. Device according to claim 1, wherein the CPU includes a memory containing a memorized value of the patient's hematocrit Hct, and wherein the input flow rate is equal to Qb×(1−Hct).

17. Device according to claim 1, wherein the CPU includes a memory containing a memorized value of the patient's hematocrit Hct and a value of the total protein concentration Cp in the blood, wherein the input flow rate is equal to Qb×(1−Hct)×(1−μ); where μ is the volumetric fraction occupied by the proteins in the patient's blood equal to Cp/1000.

18. Device for extracorporeal blood treatment comprising:
a filter having a primary and a secondary chamber separated by a semi-permeable membrane,
a withdrawal line connected to the primary chamber of the filter,
the withdrawal line operationally associated to a first means for regulating blood flow rate Qb,
a return line at the outlet of the primary chamber of the filter,
a first pre-infusion line connected to a local anticoagulation substance container and connected to the withdrawal line, and operationally associated to a second means for regulating anticoagulation liquid flow rate Qpre1,
a first post-infusion line connected to a container of a solution at least partially restoring blood ionic balance for infusing the solution in the blood and operationally associated to a third means for regulating the ionic balance restoring solution flow rate Qpost1,
an effluent line connected at the outlet of the secondary chamber of filter, connected to a drain pipe and operationally associated to a fourth means for regulating liquid effluent liquid flow rate Qeff,
wherein the device includes a CPU including a first module programmed to receive the signal output by at least one of the first, second, third and fourth means for regulating liquid flow rate and second module programmed to control at least the third means for regulating the ionic balance restoring solution flow rate Qpost1 as a function of the input flow rate equal to and chosen in the group consisting of blood flow rate Qb, plasma water blood flow rate $Q_{pw}$, plasma flow rate $Q_P$, effluent liquid flow rate Qeff and anticoagulation liquid flow rate Qpre1;
wherein the device further comprises at least one element chosen in the group consisting of:
a second pre-infusion line connected to a source of a substance to be injected in the blood containing no local anticoagulation substance, said line being operationally associated to a fifth means for regulating pre-infusion replacement solution flow rate Qpre2,
a second post-infusion line connected to a second container of a solution, said second line being connected to the return line and to a sixth means for regulating post-infusion replacement solution flow rate Qpost2,
an input line connecting a source of dialysis liquid to the secondary chamber of filter and a seventh means for regulating dialysis liquid flow rate Qdial operationally associated to said input line,
an additional CPU module to control the fourth means for regulating effluent liquid flow rate Qeff to produce a rate of desired weight loss of the patient or fluid removal flow rate Qwl,
the CPU first module is programmed to receive signal output by at least one means chosen in the group consisting of the fifth means, sixth means, seventh means and fourth means for regulating liquid flow rate,
the CPU second module is programmed to control at least the third means for regulating the ionic balance restoring solution flow rate Qpost1 as a function of the input flow rate equal to Qb, effluent liquid flow rate Qeff, anticoagulation liquid flow rate Qpre1, and at least one flow rate chosen in the group consisting of: pre-infusion replacement solution flow rate Qpre2, post-infusion replacement solution flow rate Qpost2, dialysis liquid flow rate Qdial and fluid removal flow rate Qwl.

19. Device for extracorporeal blood treatment comprising:
a filter having a primary and a secondary chamber separated by a semi-permeable membrane,
a withdrawal line connected to the primary chamber of the filter,
the withdrawal line operationally associated to a first means for regulating blood flow rate Qb,
a return line at the outlet of the primary chamber of the filter,
a first pre-infusion line connected to a local anticoagulation substance container and connected to the withdrawal line, and operationally associated to a second means for regulating anticoagulation liquid flow rate Qpre1,
a first post-infusion line connected to a container of a solution at least partially restoring blood ionic balance for infusing the solution in the blood and operationally associated to a third means for regulating the ionic balance restoring solution flow rate Qpost1,
an effluent line connected at the outlet of the secondary chamber of filter, connected to a drain pipe and operationally associated to a fourth means for regulating liquid effluent liquid flow rate Qeff,
wherein the device includes a CPU including a first module programmed to receive the signal output by at least one of the first, second, third and fourth means for regulating liquid flow rate and second module programmed to control at least the third means for regulating the ionic balance restoring solution flow rate Qpost1 as a function of the input flow rate equal to and chosen in the group consisting of blood flow rate Qb, plasma water blood flow rate $Q_{pw}$, plasma flow rate $Q_p$, effluent liquid flow rate Qeff and anticoagulation liquid flow rate Qpre1;
wherein the CPU includes a memory containing the value of parameter K0xS of filter, K0xS being the product of the filter transfer coefficient K0 and the effective filter exchange surface S, and wherein CPU second module is programmed to control at least the third means for regulating the ionic balance restoring solution flow rate Qpost1 as a function of input flow rate equal to blood flow rate Qb, anticoagulation liquid flow rate Qpre1, pre-infusion replacement solution flow rate Qpre2, effluent liquid flow rate Qeff and parameter K0xS.

20. Device for extracorporeal blood treatment comprising:
a filter having a primary and a secondary chamber separated by a semi-permeable membrane,
a withdrawal line connected to the primary chamber of the filter,
the withdrawal line operationally associated to a first means for regulating blood flow rate Qb,
a return line at the outlet of the primary chamber of the filter,
a first pre-infusion line connected to a local anticoagulation substance container and connected to the withdrawal line, and operationally associated to a second means for regulating anticoagulation liquid flow rate Qpre1,
a first post-infusion line connected to a container of a solution at least partially restoring blood ionic balance for infusing the solution in the blood and operationally associated to a third means for regulating the ionic balance restoring solution flow rate Qpost1,
an effluent line connected at the outlet of the secondary chamber of filter, connected to a drain pipe and operationally associated to a fourth means for regulating liquid effluent liquid flow rate Qeff,
wherein the device includes a CPU including a first module programmed to receive the signal output by at least one of the first, second, third and fourth means for regulating liquid flow rate and second module programmed to control at least the third means for regulating the ionic balance restoring solution flow rate Qpost1 as a function of the input flow rate equal to and chosen in the group consisting of: blood flow rate Qb, plasma water blood flow rate $Q_{pw}$, plasma flow rate $Q_p$, effluent liquid flow rate Qeff and anticoagulation liquid flow rate Qpre1;
the device further comprising the following elements:
a second pre-infusion line connected to a source of a substance to be injected in the blood containing no local anticoagulation substance, said line being operationally associated to a fifth means for regulating pre-infusion replacement solution flow rate Qpre2,
an input line connecting a source of dialysis liquid to secondary chamber of filter, and a seventh means for regulating dialysis liquid flow rate Qdial operationally associated to said input line,
and wherein the CPU includes a memory containing the value of a parameter K0xS of the filter, K0S being the product of a filter transfer coefficient K0 and a filter effective exchange surface area S, and wherein CPU second module is programmed to control at least the third means for regulating the ionic balance restoring solution flow rate Qpost1 as a function of the input flow rate equal to Qb, anticoagulation liquid flow rate Qpre1, and at least one of the flow rates chosen in the group consisting of: pre-infusion replacement solution flow rate Qpre2, effluent liquid flow rate Qeff, dialysis liquid flow rate Qdial and the K0S parameter.

* * * * *

UNITED STATES PATENT AND TRADEMARK OFFICE
CERTIFICATE OF CORRECTION

Page 1 of 1

PATENT NO. : 8,668,825 B2
APPLICATION NO. : 13/062892
DATED : March 11, 2014
INVENTOR(S) : Dominique Pouchoulin and Jacques Chevallet It is certified that error appears in the above-identified patent and that said Letters Patent is hereby corrected as shown below:

In the Claims:

At column 21 line 30, in Claim 8, after "NT = K0×S/Qb," and before "Qp being the plasma flow rate,", please insert -- Qpw being the plasma water flow rate, --.

Signed and Sealed this
Seventeenth Day of June, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,668,825 B2  
APPLICATION NO. : 13/062892  
DATED : March 11, 2014  
INVENTOR(S) : Pouchoulin et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 259 days.

Signed and Sealed this

Twenty-ninth Day of September, 2015

Michelle K. Lee
*Director of the United States Patent and Trademark Office*